United States Patent [19]

Danielson

[11] Patent Number: 4,920,082

[45] Date of Patent: Apr. 24, 1990

[54] GLASSES EXHIBITING CONTROLLED FLUORIDE RELEASE

[75] Inventor: Paul S. Danielson, Corning, N.Y.

[73] Assignee: Corning Incorporated, Corning, N.Y.

[21] Appl. No.: 427,181

[22] Filed: Oct. 25, 1989

Related U.S. Application Data

[63] Continuation-in-part of Ser. No. 304,014, Jan. 30, 1989, abandoned.

[51] Int. Cl.$^5$ ............................................. C03C 3/118
[52] U.S. Cl. .................................................... 501/59
[58] Field of Search ........................................ 501/59

[56] References Cited

U.S. PATENT DOCUMENTS

| | | | |
|---|---|---|---|
| 2,393,449 | 1/1946 | Armistead | 501/59 |
| 3,716,385 | 2/1973 | Ritzi | 501/59 |
| 4,412,015 | 10/1983 | Lustgarden et al. | 501/59 |

OTHER PUBLICATIONS

Bowen, R. L. et al., "X-Ray Opaque Reinforcing Fillers for Composite Materials", Journal of Dental Research, Jan.-Feb. 1969, pp. 79-82.

Bowen, R. L., et al.; "A New Series of X-Ray-Opaque Reinforcing Fillers for Composite Materials"; Journal of Dental Research, Jan.-Feb. 1972, pp. 177-182.

*Primary Examiner*—Mark L. Bell
*Attorney, Agent, or Firm*—Clinton S. Janes, Jr.

[57] ABSTRACT

This invention is directed to the preparation of fluoride-containing glasses wherein, when exposed to aqueous solutions, fluoride will be leached therefrom in a controlled manner over a long period of time and which can be melted and formed with little loss of fluorine through volatilization. The glasses are essentially free from alkali metal oxides and heavy toxic metals and consist essentially, in weight percent, of:

$SiO_2$: 41.4–55.9
BaO: 24.7–33.6
$Al_2O_3$: 5.6–11
$B_2O_3$: 6.5–10.3
F: 3–6

6 Claims, No Drawings

GLASSES EXHIBITING CONTROLLED FLUORIDE RELEASE

This application is a continuation-in-part of Ser. No. 07/304,014, filed Jan. 30, 1989, now abandoned.

RELATED APPLICATION

U.S. application Ser. No. 07/304,043, filed concurrently with U.S. application Ser. No. 07/304,014 by Paul D. Hammesfahr, Paul S. Danielson, and Robert C. Campbell under the title RADIOPAQUE FLUORIDE RELEASING VLC DENTAL COMPOSITES AND THE USE OF SPECIFIC FILLERS THEREIN, is directed to the use of glass fillers in polymeric composites, such as urethane composites, designed for dental restoratives.

BACKGROUND OF THE INVENTION

Fluoride-containing glasses are well known to the art; fluoride-containing glasses wherein the fluoride ion can be leached out in an aqueous environment are likewise well known to the art. In general, however, these latter glasses have exhibited an irregular rate of fluoride release; that is, exposure to an aqueous environment resulted in a relatively large initial release of fluoride ion with little subsequent release after a short period of time. Furthermore, the conventional fluoride-containing glasses of commerce have been subjected to high volatilization losses of fluorine during melting. Such losses are not only wasteful from an economic point of view, but also are hazardous to the surrounding environment, requiring expensive equipment and processes to prevent air pollution and water contamination.

Therefore, the principal objective of the present invention was to prepare fluoride-containing glass compositions wherein the fluoride ion will be leached therefrom in a controlled, relatively constant rate over a substantial period of time upon exposure to an aqueous environment, but with essentially no development of porosity or other physical breakdown effect, and which can be melted and formed employing glassmaking practices conventional in the art with relatively low volatilization of fluorine.

SUMMARY OF THE INVENTION

I have been able to achieve that objective by compounding glass compositions essentially free from alkali metal oxides and preferably also substantially free from heavy toxic metals, such as arsenic, mercury, cadmium, and lead, inasmuch as some portion thereof may leach out with the fluoride. Thus, the inventive glasses consist essentially, as analyzed in terms of weight percent, of:

$SiO_2$: 41.4–55.9
BaO: 24.7–33.6
$Al_2O_3$: 5.6–11
$B_2O_3$: 6.5–10.3
F: 3–6

The fluoride component is most conveniently supplied to the precursor glass batch in the form of $AlF_3$ and/or $BaF_2$; the retention of fluoride appearing to be enhanced when supplied as $BaF_2$. Furthermore, the loss of fluoride during melting of the batch materials appears to be less in glasses of higher BaO contents. Batch melting temperatures of about 1300°–1400° C. have proven operable; losses of fluorine through volatilization at those temperatures customarily being less than 25% and, most desirably, less than 10%.

The extent of fluoride released (leached) from the inventive glasses upon exposure to an aqueous solution appears to be closely related to the concentrations of $Al_2O_3$ and BaO present therein. To illustrate, increased fluoride release has been observed in glasses with lower $Al_2O_3$ and/or higher BaO levels. Therefore, the preferred compositions will contain no more than about 8% $Al_2O_3$ nor less than about 25% BaO. This difference in rate of release through composition control provides the opportunity to readily adjust and, hence, carefully meter the release of fluoride from the glass.

The concentration of $B_2O_3$ also plays a substantive role in controlling the release of fluoride. Thus, as the level of $B_2O_3$ is raised, the amount of fluoride release is likewise increased. This action provides yet another lever in regulating the activity of fluoride. Nevertheless, concentrations of $B_2O_3$ in excess of the designated range hazard the development of opacity in the glass.

Compatible divalent metal oxides such as SrO and ZnO may be substituted in part for BaO, but not without a substantive effect upon the melting behavior of the glass or upon the physical properties of the resulting glass. To illustrate:

Whereas phase separation is present in glasses containing BaO only, the amount of phase separation, as estimated visually from the level of opacity observed in the glass at room temperature, appears to rise dramatically when BaO is replaced by SrO. Hence, an inspection of annealed bodies of glass indicated a progression from translucent to fully opaque as greater substitutions of SrO for BaO are made. Transmission electron micrographs of fractured glass surfaces have revealed the presence of phase separated droplets in all of the glasses. In the glasses containing BaO within the above-cited ranges only, however, not only are fewer droplets seen, but also the size of the droplets ranges about 500–1400 Å. By comparison, not only are more droplets observed in those glasses containing SrO, but also the sizes thereof range up to 2000 Å and larger in glasses with full substitution of SrO for BaO. The greater number and larger size of the droplets in the SrO-containing glasses explain the increased opacity noted in those glass compositions.

One proposed utility for the inventive glasses has been as fillers for dental restorative materials. As is explained in U.S. Pat. No. 4,431,420, one of the several vital characteristics which dental restorative materials must exhibit is a visual appearance similar to that of tooth structure. One critical feature in the simulation of tooth appearance is the presence of translucency in the material. That is, the material cannot be densely opaque. Therefore, to assure acceptable translucency in the inventive materials, thereby rendering them suitable for that application, the size of the phase separated droplets will not exceed about 1400 Å. Accordingly, the most preferred materials will exhibit translucency.

Whereas various properties of the glasses, such as the softening, annealing, and strain points, the densities, and the coefficients of thermal expansion, can be varied through additions of SrO, its presence does not appear to assist in controlling the rate at which fluoride is leached out of the glass in aqueous solutions. Accordingly, substitutions of SrO for BaO will normally be limited to not more than about one-half on a molar basis.

With regard to ZnO, experience has demonstrated that the inclusion of substantial amounts leads to significant increases in fluorine volatilization during melting of the batch. Consequently, substitutions of ZnO for BaO will customarily be limited to no more than about one-third on a molar basis and, preferably, no more than 7% by weight.

Minor amounts of extraneous additions, such as $SnO_2$ and $P_2O_5$, may be present at levels not exceeding about 5% by weight total without adversely affecting the leaching character of the glass. Alkali metal oxides, however, will preferably be absent, because they reduce the overall chemical durability of the glass and cause the rapid leaching of fluoride.

PRIOR ART

U.S. Pat. No. 3,326,703 described the preparation of heat absorbing glasses consisting essentially, in weight percent, of 35–70% $SiO_2$, 5–30% $Al_2O_3$, 4–25% $B_2O_3$, 2–25% ZnO and/or CdO, 5–30% CaO and/or MgO and/or BaO, 0.25–5% FeO, 0–1% $Li_2O$ and/or $Na_2O$ and/or $K_2O$, and 0–3% F. No reference is made to fluoride leaching; fluoride is merely an optional component. Even excluding FeO, no working example had a composition coming within the ranges of the present inventive glasses.

U.S. Pat. No. 3,716,385 disclosed the production of optical glasses consisting essentially, in weight percent, of 15–45% $SiO_2$, 0–15% $B_2O_3$, 30–47% $SiO_2+B_2O_3$, 25–56% BaO, 0–10% $BaF_2$, 35–56% $BaO+BaF_2$, and 3–18% $AlF_3$. No mention is made of fluoride leaching and none of the exemplary glasses provided in the patent is even relatively close in composition to the present inventive glasses.

U.S. Pat. No. 4,358,549 was directed to dental filling compositions consisting essentially, in weight percent, of 45–65% $SiO_2$, 20–35% ZnO, 3–15% $B_2O_3$, $\geq 2\%$ $AlF_3$, 0–10% $Al_2O_3$, and 0–3% alkali metal oxides or alkaline earth metal oxides. No indication is given that fluoride can be leached from the glasses and the ZnO content is substantially greater than that which can be tolerated in the present inventive glasses.

U.S. Pat. No. 4,746,868 was drawn to the development of visible light activated cavity liners for use in dental restoration. The liner provided a source of leachable calcium and fluoride and was comprised of a photopolymerizable matrix material, a photo initiator, a reducing agent, a synthetic hydroxyapatite filler, and a powdered glass ionomer filler. The single powdered glass composition provide consisted, in weight percent, of 31% $SiO_2$, 24% $Al_2O_3$, 15% $AlPO_4$, 12% $AlF_3$, and 18% sodium aluminum fluoride. That composition is far removed from the present inventive glasses.

U.S. Pat. No. 4,775,646 was concerned with bioactive glasses having a base composition consisting, in weight percent, of 46.1% $SiO_2$, 2.6% $P_2O_5$, 26.9% CaO, and 24.4% $Na_2O$, wherein about 40 mole percent of the CaO is replaced with $CaF_2$. The glasses are employed as prosthetic implants and demonstrate the ability to chemically bond to living tissue. They also crystallize in situ over time with the formation of apatite-type crystals. The compositions are quite remote from the present inventive glasses, and there is no reference to controlled leaching of fluoride.

U.S. Pat. No. 4,797,431 was directed to the preparation of optically translucent dental restorative materials which exhibit radiopacity. The materials were prepared by reacting an organic polymer containing free carboxyl groups with an acid- or alkali-leachable source of polyvalent metal ions in the presence of water and $SrF_2$, the $SrF_2$ providing the radiopacity. The leachable source of polyvalent metal ions was a glass consisting essentially, in weight percent, of 15–33% $SrF_2$, 28–38% $Al_2O_3$, 25–30% $SiO_2$, not more than 25% CaO, and 0–9% $P_2O_5$. Those glass compositions are far removed from those of the present invention and no mention is made of controllably leaching fluoride from the glasses. On the contrary, polyvalent metal ions are leached from the glasses.

R. L. Bowen and G. W. Cleek in "X-ray Opaque Reinforcing Fillers for Composite Materials," *Journal of Dental Research*, January-February 1969, pages 79–82, discussed the preparation of glasses suitable for use as radiopaque fillers for dental restorative materials, those glasses being composed primarily of $Al_2O_3$, BaO, $BaF_2$, $B_2O_3$, and $SiO_2$. There was no reference to controllably leaching fluoride from the glasses and the compositions of the reported glasses are generally lower in $SiO_2$ than the minimum required in the present inventive glasses.

R. L. Bowen and G. W. Cleek in "A New Series of X-Ray-Opaque Reinforcing Fillers for Composite Materials," *Journal of Dental Research*, January-February 1972, pages 177–182, described a further series of glasses suitable for use as radiopaque fillers for dental restorative materials, those glasses being composed primarily of $Al_2P_3$, BaO, $B_2O_3$, and $SiO_2$, with various optional additives including $BaF_2$ and ZnO. Again, no mention is made of controllably leaching fluoride from the glasses; fluoride is merely an optional component. The glasses recited have compositions outside of the ranges required in the present inventive glasses.

G. D. Derkson, P. J. Poon, and A. S. Richardson in "Fluoride Release from a Silicophosphate Cement with Added Fluoride," *Journal of Dental Research*, 61, No. 5, pages 660–664, May 1982, disclosed increasing the rate of fluoride release from fluoride-containing cements used in dental cements and restorative materials. The authors added 10% by weight of $Na_2SiF_6$ to a commercial dental cement. Although leaching of fluoride from a dental cement is described, the thrust of the work was to increase the rate of fluoride release; there is no reference to providing compositions wherein the rate of fluoride leaching would be relatively constant. Moreover, the present inventive glasses are most preferably essentially free from alkali metals, whereas the authors here purposefully added sodium ions.

M. L. Swartz, R. W. Phillips, and H. E. Clark in "Long-Term F Release from Glass Ionomer Cements," *Journal of Dental Research*, 63, No. 2, pages 158–160, February 1984, reported on experiments to study the rate of and the longevity of fluoride release from various silicate, silicophosphate, and fluoride-containing polycarboxylate glass ionomer filling cements. No glass composition data are furnished.

DESCRIPTION OF PREFERRED EMBODIMENTS

Table I records a group of glasses illustrating the composition parameters of the present invention. The oxide components are recited in terms of parts by weight, as calculated from the glass batch materials, and, because it is not known with which cation(s) the fluoride is combined in the glass, it is merely reported in terms of F. The fluoride is reported in terms of its presence in the batch, i.e., F(B), and as analyzed in the glass prepared from the batch, i.e., F(A), thereby providing evidence of the relatively low loss of fluoride through volatilization during melting of the batch. Inasmuch as the sum of the individual ingredients closely approximates 100, for all practical purposes the values listed in Table I can be deemed to reflect weight percent.

The actual batch materials for the oxide constituents can comprise either the oxides, themselves, or other compounds which, when melted together, will be converted into the desired oxide in the proper proportion. For example, $BaCO_3$ may supply the source of BaO. As was noted above, fluoride was conveniently introduced in the form of $BaF_2$ or $AlF_3$, the former constituting the preferred batch ingredient.

The batch ingredients were compounded, thoroughly tumble-mixed together to assist in securing a homogeneous melt, and then charged into platinum crucibles. After placing lids thereon, the crucibles were introduced into a furnace operating at about 1400° C., held therewithin for at least four (4) hours, depending upon the weight of the batch, to achieve good melting. Thus, longer furnace times are required with large batches to assure homogeneous melts. Thereafter, the crucibles were removed from the furnace and the melts poured as a relatively fine stream into a bath of cold tap water. This practice, termed drigaging, breaks up the glass stream into small particles which can be readily milled or otherwise comminuted to very small dimensions. The drigaged samples were reduced to powders having an average diameter of about 5–15 microns by ballmilling in $Al_2O_3$ containers with $Al_2O_3$ milling media.

A screening test was devised to provide an estimate of the amount of fluoride leached from the inventive glasses. This test involved immersing 1 gram samples of powdered glass into 100 ml distilled water for 25 hours at room temperature and analyzing the resulting solution for fluoride, the concentration present therein being reported in terms of micrograms/ml. The results of that testing are recorded in the following tables as the release of fluoride, i.e., F(R).

TABLE I

|  | 1 | 2 | 3 | 4 | 5 | 6 | 7 |
|---|---|---|---|---|---|---|---|
| $SiO_2$ | 49.0 | 47.4 | 48.7 | 46.9 | 47.2 | 44.1 | 47.4 |
| $Al_2O_3$ | 8.3 | 8.0 | 8.3 | 8.0 | 8.1 | 7.5 | 8.0 |
| $B_2O_3$ | 8.4 | 8.3 | 8.3 | 8.0 | 8.1 | 7.5 | 8.1 |
| BaO | 30.3 | 29.3 | 30.1 | 29.0 | 29.2 | 27.2 | 29.3 |
| SrO* | 0.3 | — | 0.5 | 0.5 | 0.3 | — | — |
| F(B) | 3.6 | 7.1 | 3.9 | 7.6 | 7.3 | 13.7 | 7.1 |
| F(A) | 3.1 | 4.6 | 3.6 | 4.6 | 4.5 | 5.4 | — |
| F(R) | 3.4 | 6.0 | 3.2 | 6.6 | 7.0 | 9.0 | 3.1 |

|  | 8 | 9 | 10 | 11 | 12 | 13 | 14 |
|---|---|---|---|---|---|---|---|
| $SiO_2$ | 46.4 | 45.4 | 43.4 | 45.4 | 45.4 | 43.3 | 41.4 |
| $Al_2O_3$ | 8.0 | 8.0 | 8.0 | 8.0 | 8.0 | 8.0 | 8.0 |
| $B_2O_3$ | 8.1 | 8.1 | 8.1 | 8.1 | 8.1 | 8.1 | 8.1 |
| BaO | 29.3 | 29.3 | 29.3 | 29.3 | 29.3 | 29.3 | 29.3 |
| F(B) | 7.1 | 7.1 | 7.1 | 7.1 | 7.1 | 7.1 | 7.1 |
| F(A) |  |  |  |  |  |  |  |
| $P_2O_5$ | 1.0 | 2.0 | 4.0 | — | — | 2.0 | 4.0 |
| ZnO | — | — | — | 2.0 | — | 2.0 | 2.0 |
| $SnO_2$ | — | — | — | — | 2.0 | — | — |
| F(R) | 4.5 | 4.5 | 3.7 | 3.0 | 3.0 | 3.2 | 2.6 |

*SrO was a contaminant in the BaO batch material

Table II recites a second group of glasses, the compositions of which are reported in like manner to those in Table I. In each batch the fluoride component was introduced in the form of $BaF_2$, the amount of that component being recorded in the Table. Table II also lists the total BaO concentration, i.e., BaO(T), as calculated from the batch materials, along with the batched fluoride, as calculated from the $BaF_2$, and the fluoride as analyzed in the glass. The batch materials were compounded, mixed, melted, drigaged, and powdered in like manner to the procedure described above with respect to the glasses reported in Table I. Fluoride release in the abovedescribed aqueous solution test is also recorded.

TABLE II

|  | 15 | 16 | 17 | 18 | 19 |
|---|---|---|---|---|---|
| $SiO_2$ | 49.1 | 51.7 | 45.9 | 49.3 | 43.6 |
| $Al_2O_3$ | 8.3 | 11.0 | 10.5 | 10.8 | 10.3 |
| $B_2O_3$ | 8.4 | 6.8 | 6.5 | 10.1 | 9.6 |
| BaO | 4.3 | — | 8.3 | — | 8.2 |
| $BaF_2$ | 29.9 | 30.5 | 28.9 | 29.9 | 28.4 |
| BaO(T) | 30.4 | 26.6 | 33.6 | 26.1 | 33.0 |
| F(B) | 6.5 | 6.6 | 6.3 | 6.5 | 6.2 |
| F(A) | 5.4 | 5.0 | 6.0 | 5.3 | 5.7 |
| F(R) | 4.2 | 2.3 | 2.9 | 3.3 | 3.6 |

|  | 20 | 21 | 22 | 23 |
|---|---|---|---|---|
| $SiO_2$ | 55.9 | 49.7 | 53.3 | 47.3 |
| $Al_2O_3$ | 6.1 | 5.8 | 6.0 | 5.7 |
| $B_2O_3$ | 7.0 | 6.6 | 10.3 | 9.8 |
| BaO | — | 8.5 | — | 8.3 |
| $BaF_2$ | 31.1 | 29.5 | 30.5 | 28.9 |
| BaO(T) | 27.2 | 34.3 | 26.7 | 33.6 |
| F(B) | 6.7 | 6.4 | 6.6 | 6.3 |
| F(A) | 5.0 | 5.7 | 4.6 | 5.3 |
| F(R) | 10.7 | 17.0 | 10.5 | 20.8 |

Table III records a series of glass compositions wherein SrO replaced BaO in stepwise fashion. The fluoride content is tabulated in terms of weight percent as calculated from the batch materials and as analyzed in the glass. Table IIIA recites the proportions of BaO and SrO in terms of mole percent. Again, the batches were compounded, mixed, melted, drigaged, and powdered in like manner to the compositions reported in Table I. Fluoride release in the above-described aqueous solution test is also reported.

The glasses of Table III also illustrate the increase in phase separation occurring in the glass when SrO is substituted for BaO, as estimated by visual observation of the glass at room temperature. Thus, an annealed slab of solely BaO-containing glass appears translucent or very weakly opaque to the eye. Upon replacement with SrO, the glass develops greater opacity until, upon complete substitution, the glass is totally opaque. Finally, Table III lists measurements of phase separated droplet sizes observed in transmission electron micrographs (TEM) of fractured glass surfaces.

TABLE III

|  | 24 | 25 | 26 | 27 | 28 |
|---|---|---|---|---|---|
| $SiO_2$ | 47.1 | 47.9 | 48.8 | 50.0 | 52.0 |
| $Al_2O_3$ | 7.9 | 8.0 | 8.2 | 8.4 | 8.7 |
| $B_2O_3$ | 8.1 | 8.2 | 8.4 | 8.6 | 8.9 |
| BaO | 29.6 | 24.7 | 19.5 | 12.4 | — |
| SrO | — | 3.7 | 7.5 | 12.9 | 22.1 |
| F(B) | 7.3 | 7.4 | 7.5 | 7.6 | 7.9 |
| F(A) | 5.4 | 5.3 | 5.6 | 5.7 | 5.8 |
| F(R) | 3.0 | 6.1 | 6.2 | 5.6 | 5.2 |
| Opacity | Weak | Weak | Medium | Medium | Opaque |
| TEM | 500–1400Å | — | 800–2000Å | — | 2000Å |

TABLE IIIA

|  | 24 | 25 | 26 | 27 | 28 |
|---|---|---|---|---|---|
| BaO | 16.5 | 13.5 | 10.5 | 6.5 | — |
| SrO | — | 3.0 | 6.0 | 10.0 | 16.5 |

Table IV lists a number of glass compositions wherein $ZnF_2$ was substituted for $BaF_2$ in stepwise fashion. The batched fluoride was calculated from $ZnF_2$ and $BaF_2$. The analyzed fluoride is also reported.

Table IVA records the proportions of $ZnF_2$ and $BaF_2$ in terms of mole percent. Yet again, the batches were compounded, mixed, melted, drigaged, and powdered in like manner to the compositions reported in Table I.

TABLE IV

|  | 29 | 30 | 31 | 32 | 33 |
|---|---|---|---|---|---|
| $SiO_2$ | 48.6 | 50.3 | 52.2 | 54.2 | 56.7 |
| $Al_2O_3$ | 8.1 | 8.4 | 8.7 | 9.1 | 9.5 |
| $B_2O_3$ | 8.4 | 8.7 | 9.0 | 9.3 | 9.8 |
| $BaF_2$ | 34.9 | 27.4 | 19.3 | 10.6 | — |
| $ZnF_2$ | — | 5.2 | 10.7 | 16.7 | 24.1 |
| F(B) | 7.3 | 7.6 | 7.9 | 8.2 | 8.5 |
| F(A) | 5.6 | 5.2 | 4.4 | 3.0 | 1.27 |

|  | 34 | 35 | 36 | 37 |
|---|---|---|---|---|
| $SiO_2$ | 46.7 | 49.3 | 52.2 | 55.4 |
| $Al_2O_3$ | 5.6 | 5.9 | 6.2 | 6.6 |
| $B_2O_3$ | 9.7 | 10.3 | 10.9 | 11.5 |
| $BaF_2$ | 37.9 | 26.8 | 14.0 | — |
| $ZnF_2$ | — | 7.8 | 16.7 | 26.5 |
| F(B) | 7.9 | 8.3 | 8.8 | 9.4 |
| F(A) | 5.4 | 4.4 | 3.0 | 1.25 |

TABLE IVA

|  | 29 | 30 | 31 | 32 | 33 | 34 | 35 | 36 | 37 |
|---|---|---|---|---|---|---|---|---|---|
| $BaF_2$ | 16.5 | 12.5 | 8.5 | 4.5 | — | 18.2 | 12.2 | 6.0 | — |
| $ZnF_2$ | — | 4.0 | 8.0 | 12.0 | 16.5 | — | 6.0 | 12.2 | 18.2 |

In order to assess the influences of batch materials and melting times and temperatures upon fluoride retention in the glass, the six glass compositions recorded in Table V were examined. Thus, comparisons were made between the use of $BaF_2$ and $AlF_3$ as sources of fluoride while varying the times (2, 3, and 4 hours) and temperatures (1300° C. and 1400° C.) of melting. The concentrations of fluoride in the batch, i.e., F(B) as calculated from $BaF_2$ and $AlF_3$, and the analyzed values of fluoride in the glass, i.e., F(A), are recited.

TABLE V

|  | 38 | 39 | 40 | 41 | 42 | 43 |
|---|---|---|---|---|---|---|
| $SiO_2$ | 47.4 | 47.4 | 47.4 | 46.9 | 46.9 | 46.9 |
| $Al_2O_3$ | 8.0 | 8.0 | 8.0 | — | — | — |
| $B_2O_3$ | 8.1 | 8.1 | 8.1 | 8.0 | 8.0 | 8.0 |
| $BaF_2$ | 33.6 | 33.6 | 33.6 | — | — | — |
| BaO | — | — | — | 29.0 | 29.0 | 29.0 |
| $AlF_3$ | — | — | — | 13.6 | 13.6 | 13.6 |
| F(B) | 7.1 | 7.1 | 7.1 | 7.6 | 7.6 | 7.6 |
| 1300° C. | 2 hrs | 3 hrs | 4 hrs | 2 hrs | 3 hrs | 4 hrs |
| F(A) | 5.7 | 5.5 | 5.5 | 5.5 | 5.4 | 5.4 |
| 1400° C. | 2 hrs | 3 hrs | 4 hrs | 2 hrs | 3 hrs | 4 hrs |
| F(A) | 5.4 | 5.3 | 5.2 | 5.2 | 5.1 | 5.1 |

In order to investigate the effect upon fluoride release from the inventive glasses when exposed to a subsequent heat treatment, the milled, drigaged powders of Examples 1-6 were heated to 740° C. and maintained at that temperature for 45 minutes. A comparison of the fluoride release in the base powders, i.e., F(R), with the fluoride release in the heat treated powders, i.e., F(HT), is reported in Table VI.

TABLE VI

|  | 1 | 2 | 3 | 4 | 5 | 6 |
|---|---|---|---|---|---|---|
| F(R) | 3.4 | 6.0 | 3.2 | 6.6 | 7.0 | 9.0 |
| F(HT) | 3.0 | 14.0 | 6.0 | 13.0 | 13.0 | 5.0 |

A study of the above Tables points up several features of the present invention with respect to volatilization of fluorine during melting of the batch and the release of fluoride from the glasses when exposed to aqueous solutions.

First, the total fluoride that can be retained in the glass is about 7% by weight;

Second, batch levels of fluoride in excess of about 8% by weight are ineffective in promoting increased fluoride retention, inasmuch as much higher levels appear to result in greater volatilization of fluorine, with no additional fluoride being retained in the glass;

Third, the substitution of Zn for Ba dramatically increases the rate and amount of fluorine volatilization;

Fourth, volatilization of fluorine appears to take place relatively early in the melting process; that is, very little decrease in fluoride retained in the glass is seen after two hours;

Fifth, higher melting temperatures foster greater volatilization of fluorine;

Sixth, whereas higher levels of fluoride can be batched with $AlF_3$ and $ZnF_2$, volatilization of fluorine during melting of the batch is considerably less when $BaF_2$ comprises the fluoride-containing batch ingredient; that is, higher BaO contents appear to aid in fluorine retention;

Seventh, in general, higher levels of fluoride in the glass lead to greater sustained release of fluoride when the glass is contacted with an aqueous solution;

Eighth, in general, glasses of lower $Al_2O_3$ content will demonstrate greater release of fluoride when immersed in an aqueous solution, as will glasses of higher BaO concentrations;

Ninth, in general, additional heat treatment of the inventive glasses does not seriously impact the release of fluoride therefrom; this lack of substantial effect has been conjectured as being derived from the fact that the glasses are phase separated, the resulting microstructure being relatively immune to the effects of heat treatment; and Tenth, the presence of phase separation is observed in the inventive glasses; the presence thereof greatly increasing when SrO is substituted for BaO.

To illustrate the long term fluoride release capability of the present inventive glasses, several of the glasses reported in Tables I, II, and III were subjected to a Soxhlet Extraction utilizing distilled water as the extractant. The amount of fluoride in the aqueous extraction solution was analyzed daily in terms of parts per million (ppm) over a period of seven days. Because of the high temperatures necessarily involved in Soxhlet Extractions, the use thereof here constitutes a very accelerated test of fluoride release in water, when compared with exposure to water under normal ambient conditions. Nevertheless, the procedure does provide a rational estimate as to the behavior of a glass under less severe temperature conditions.

In the following tests recorded in Table VII, 10 gram samples of the powdered glasses were used and the fluoride release measured employing a fluoride ion selective electrode with four point calibration, viz., 1, 10, 25, and 100 ppm standards.

TABLE VII

|  | 2 | 3 | 4 | 5 | 6 |
|---|---|---|---|---|---|
| Day 1 | 27.038 | 201.160 | 37.616 | 36.002 | 42.769 |
| Day 2 | 9.804 | 195.870 | 13.188 | 13.497 | 20.928 |
| Day 3 | 6.045 | 49.629 | 9.491 | 9.529 | 14.307 |
| Day 4 | 5.252 | 45.051 | 9.409 | 9.224 | 14.274 |
| Day 5 | 5.740 | 40.607 | 9.136 | 9.174 | 14.272 |
| Day 6 | 6.516 | 29.317 | 7.356 | 9.008 | 11.655 |

TABLE VII-continued

| | 2 | 3 | 4 | 5 | 6 |
|---|---|---|---|---|---|
| Day 7 | 4.303 | 17.996 | 5.870 | 6.480 | 7.355 |

As is readily apparent from Table VII, after an initial substantial release of fluoride the inventive glasses settle to a release level of about 25% of that of the original release, and that level is maintained for several days thereafter.

In contrast, an alkali metal-, alkaline earth metal-containing aluminoborofluorosilicate opal glass of the type described in U.S. Pat. No. 4,080,215 and marketed by Corning Glass Works, Corning, N.Y., under Code 6005 having an analyzed fluoride content of about 5%, when subjected to Soxhlet Extraction, exhibited the following release of fluoride, in parts per million:

Day 1: 130
Day 2: 2.9
Day 3: 2.2
Day 4: 2.3
Day 5: 2.3
Day 6: 2.3
Day 7: 2.3

It is immediately evident that, after the initial release of fluoride, the glass becomes quite resistant to attack by water, the release of fluoride becoming virtually inconsequential. It is conjectured that the initial large extraction of fluoride results from alkali metal fluoride being leached out of the glass. The remaining small amount of fluoride is rather tightly bonded to the other glass components.

I claim:

1. A translucent, phase separated, fluoride-containing glass wherein the phase separated droplets do not exceed about 1400Å in size and wherein, upon exposure to an aqueous environment, fluoride ions will be released therefrom at a controlled, relatively constant rate over a substantial period of time, but with essentially no development of porosity or other physical breakdown effect, and which can be melted and formed with relatively low volatilization of fluorine, said glass being essentially free of alkali metal oxides and heavy toxic metals and consisting essentially, expressed in terms of weight percent of:

$SiO_2$: 41.4–55.9
BaO: 24.7–33.6
$Al_2O_3$: 5.6–11
$B_2O_3$: 6.5–10.3
F: 3–6.

2. A glass according to claim 1 wherein the $Al_2O_3$ content ranges between 4–8%.

3. A glass according to claim 1 wherein up to one-half on a molar basis of BaO is replaced with SrO.

4. A glass according to claim 1 wherein up to one-third on a molar basis of BaO is replaced with ZnO.

5. A glass according to claim 1 wherein said heavy toxic metals are selected from the group consisting of arsenic, cadmium, lead, and mercury.

6. A glass according to claim 1 wherein said fluoride is included in the composition through the use of a batch material selected from the group of $AlF_3$ and $BaF_2$.

* * * * *